US005487756A

United States Patent [19]
Kallesoe et al.

[11] Patent Number: 5,487,756
[45] Date of Patent: Jan. 30, 1996

[54] IMPLANTABLE CUFF HAVING IMPROVED CLOSURE

[75] Inventors: Klaus Kallesoe, Burnaby; Joaquín A. Hoffer, Anmore; Kevin Strange, Port Moody; Ignacio Valenzuela, Richmond, all of Canada

[73] Assignee: Simon Fraser University, Burnaby, Canada

[21] Appl. No.: 363,334

[22] Filed: Dec. 23, 1994

[51] Int. Cl.$^6$ ............................... A61N 1/05; A61N 1/04
[52] U.S. Cl. ........................... 607/118; 128/639; 128/642
[58] Field of Search ..................................... 607/115, 116, 607/117, 118; 128/639, 642, 644, 734, 693

[56] References Cited

U.S. PATENT DOCUMENTS

| | | |
|---|---|---|
| 4,602,624 | 7/1986 | Naples . |
| 4,750,499 | 6/1988 | Hoffer . |
| 4,920,979 | 5/1990 | Bullara . |
| 4,921,479 | 5/1990 | Grayzel . |
| 4,926,875 | 5/1990 | Rabinovitz . |
| 4,940,065 | 7/1990 | Tanagho . |
| 5,199,430 | 4/1993 | Fang . |
| 5,265,608 | 11/1993 | Lee . |
| 5,282,468 | 2/1994 | Klepinski . |
| 5,289,821 | 3/1994 | Swartz . |
| 5,324,322 | 6/1994 | Grill . |
| 5,344,438 | 9/1994 | Testerman . |
| 5,358,514 | 10/1994 | Schulman . |

OTHER PUBLICATIONS

Haugland, M. K. and Hoffer, J. A. Slip information provided by nerve cuff signals: application in closed–loop control of functional electrical stimulation, *IEEE Trans. Rehab. Eng.*, vol. 2, pp. 29–36, Mar. 1994.

Hoffer, J. A. Techniques to study spinal–cord, peripheral nerve, and muscle activity in freely moving animals. in *Neuromethods, vol. 15: Neurophysiological Techniques: Application eo Neural Systems*, A. A. Boulton, G. B, Baker and C. H. Vanderwolf, editors, the Humana Press, pp. 65–145, 1990.

Hoffer, J. A. and Haugland, M. Signals from tactile sensors in glabrous skin suitable for restoring motor functions in paralyzed humans. in *Neural Prostheses: Replacing Motor Function after Disease or Disability*, R. B. Stein, P. H. Peckham, and D. Popovic, editors. Oxford Univ. Press, pp. 99–125, 1992 (copy not available).

Hoffer, J. A. and Weytjens, J. L. F. Alpha–motoneurons activity, afferent activity and muscle fiber movement simultaneously recorded from cat medial gastrocnemius muscle during posture and locomotion. *Soc. Neurosci. Abstr.* 16:891, No. 368.14, 1990.

Kallesoe K., Valenzuela I., Viberg D. and Hoffer J. A. Interfacing to single peripheral axons using flexible silicon multicontact probes. Presented at "Neural Prostheses Workshop: Motor Systems IV", Ohio, Jul. 1994.

Kostov, A., Stein, R. B., Popovic, D. and Armstrong, W. W. Improved methods for control of FES for locomotion, in *Proc. of Modeling and Control in Biomedical Systems*, Galveston, pp. 422–427, 1994.

Mortimer, J. T. Electrical excitation of nerve, in *Neural Prostheses: Fundamental Studies*, W. F. Agnew and D. B. McCreery, editors. Prentice Hall, pp. 67–84, 1990. (copy not available).

(List continued on next page.)

*Primary Examiner*—Angela Sykes
*Assistant Examiner*—Stephen Huang
*Attorney, Agent, or Firm*—Oyen Wiggs Green & Mutala

[57] ABSTRACT

An implantable cuff having an improved closure is disclosed. The closure has a set of small interdigitated tubes lying along the edges of a longitudinal slit opening in the cuff. A rod-like locking member is inserted through the interdigitated tubes to lock the cuff closed. A flexible flap attached to the inside of the cuff electrically and mechanically isolates the interior of the cuff from the exterior. The cuff has particular application as a nerve cuff for recording electrical nerve activity and for electrically stimulating nerves.

30 Claims, 9 Drawing Sheets

OTHER PUBLICATIONS

Popovic, D. B., Stein, R. B., Jovanovic, K. L., Dai, R., Kostov, A. and Armstrong, W. W. Sensory nerve recording for closed–loop control to restore motor functions. *IEEE Trans. Bio. Eng.*, vol. 40, pp. 1024–1031, Oct. 1993.

Sinkjar, T., Haugland, M. and Haase, J. The use of natural sensory nerve signals as an advanced heel–switch in drop–foot patients. in *Proc. of the 4th Vienna Workshop of FES*, pp. 134–137, 1992. (copy not available).

Stein, R. B., Peckham, P. H., and Popovic. D. (editors) *Neural Prostheses: Replacing Motor Function after Disease or Disability.* Oxford Univ. Press, 1992.

PRIOR ART

IMPLANTABLE CUFF HAVING IMPROVED CLOSURE

FIELD OF THE INVENTION

This invention relates to cuffs for surgical implantation in animals and humans. The cuffs are used to surround and enclose internal body tissues. Cuffs according to the invention have particular application as nerve cuffs and can be made electrically insulating and equipped with electrodes to electrically stimulate or record electrical activity in tissues surrounded by the cuff.

BACKGROUND OF THE INVENTION

Cuffs are used in biomedical research and in clinical applications to surround and enclose internal body tissues, such as nerves, arteries, veins, muscles, tendons, ligaments, the oesophagus, intestines, fallopian tubes and other generally tubular internal organs. The functions of cuffs can include: chemically and/or electrically isolating selected tissues from surrounding tissues; supporting electrodes for electrically interacting with tissues inside the cuff; supporting tissues; administering drugs or chemicals to tissues within the cuff; and serving as a platform for physiological experiments.

A simple form of cuff that has been widely used in the prior art comprises a section of elastic tube that is slit longitudinally. These cuffs are implanted by separating the edges of the slit to expose the interior of the cuff, placing selected tissues on the cuff and then allowing the cuff to close around the selected tissues. The cuff is then tightly closed and sealed by tying sutures around the cuff at several places along its length. Cuffs of this nature are described in Hoffer, J. A. Techniques to study spinal-cord, peripheral nerve, and muscle activity in freely moving animals. in *Neuromethods, Vol. 15: Neurophysiological Techniques: Application to Neural Systems*, A. A. Boulton, G. B. Baker and C. H. Vanderwolf, editors. The Humana Press, pp. 65–145, 1990.

The prior art cuffs described above have several disadvantages. Some of these disadvantages arise from the use of sutures to close the cuff and are as follows:

1. Braided suture material, either absorbable or non-absorbable, can easily attract and retain contaminants. The presence of such contaminants can result in local foreign body reactions.
2. Connective tissue can also grow on the sutures themselves and around the cuff, this can make removing the cuff difficult.
3. Sutures of most suture materials have a limited lifetime within the fluid environment of the body and tend to break down at the location of the knots. If the suture material breaks down the cuff can open. Many suture materials can be reliably implanted for no more than a few months.
4. A tradeoff must be made between increasing the number of closing sutures for a given length of nerve cuff to improve the electrical and mechanical isolation of the interior from the exterior, and decreasing the number of closing sutures to decrease the time, complexity, and skill required to implant the cuff on a nerve.

Stainless steel sutures are easier to clean and should survive longer in the body than sutures of other materials. However, steel sutures are generally very stiff and difficult to tie into knots. Steel sutures are also thin and sharp and can easily cause damage by cutting through tissue and/or cuff materials during or after implantation of a cuff.

The cuffs described above also have disadvantages that arise from the use of a slit tube. In some cases, such cuffs can compress the tissues inside them and/or fail to provide an effective electrical and fluid seal around the enclosed tissues. These disadvantages are particularly significant for nerve cuffs. It is especially important in a nerve recording cuff that the cuff closure in the central portion of the cuff, where the recording electrodes are located, provide a good seal so that the cuff will provide good electrical isolation. One source of problems in prior art sutured cuffs is that if the sutures do not hold the cuff tightly closed then connective tissue tends to grow into the cuff through the open longitudinal slit. This reduces the electrical and mechanical isolation of the interior of the cuff. Breakdown of the cuff seal is therefore undesirable. Some prior cuffs have a thin, flexible flap on the outside of the cuff tubing which spans the longitudinal slit. The flap is held in place over the slit by sutures which encircle the cuff. If enough sutures are used to hold the flap down along the entire length of the cuff the flap can restrict fluid movement and tissue growth through the slit.

Another source of problems is that one edge of the longitudinal slit can slip radially inward with respect to the other edge of the slit. This reduces the volume inside the cuff and can consequently compress and damage the tissues in the lumen of the cuff. Where the cuff surrounds a nerve, severe damage can result if the edges of the cuff slip, as described, and the cuff squeezes the nerve.

An alternative cuff design is described by Naples et al. U.S. Pat. No. 4,602,624. The Naples et al. cuff is formed from laminated sheets of flexible, non-conducting, material. The laminated sheets are differentially stretched in the lamination process so that the cuff tends to cuff around itself, like a rolled up carpet. A special tool is preferably used to implant the cuff. When it is in place the cuff wraps around the enclosed tissues. The Naples et al. cuff does not require sutures to keep it closed.

For nerve recording cuff applications the Naples et al. cuff has the disadvantage that it does not always provide good enough electrical isolation of the interior of the cuff. Connective tissue may grow into the seam of the cuff from both the inside and the outside of the cuff. This connective tissue could eventually provide an unwanted shunting path for current flow and may even pry the cuff open.

The Naples et al. cuff has the further disadvantages that it typically requires a special tool for implantation and it may be difficult to implant. There is no simple method to open the cuff during surgical conditions. Implanting the Naples et al. cuff around a nerve or other delicate tissue can be risky. The cuff could seriously damage a nerve if it closes before the nerve is properly located. Another potential disadvantage of the Naples et al. cuff is that it may be difficult to remove without causing tissue damage.

Prior art cuffs, as described above, have been equipped with electrodes and used for interfacing with the nervous system by recording from or stimulating neural tissues. For example, implanted nerve cuffs are used to record nerve signals from peripheral nerves in animals in a wide range of experimental conditions. Nerve cuff electrodes have been used in stimulation systems with the goal of providing partial voluntary control of muscles that were paralyzed as a result of lesions caused by spinal cord injury, stroke, or other central neurological disorders. In some cases, partial motor function can be restored by stimulating motor neurons or muscles below the level of the lesion.

Recent advances in the understanding of sensory signals recorded with nerve cuffs have led to their consideration as sources of feedback for the control of closed-loop functional electrical stimulation (FES) systems as described in Hoffer, U.S. Pat. No. 4,750,499 entitled CLOSED-LOOP, IMPLANTED-SENSOR, FUNCTIONAL ELECTRICAL STIMULATION SYSTEM FOR PARTIAL RESTORATION OF MOTOR FUNCTIONS.

SUMMARY OF THE INVENTION

This invention provides an implantable cuff having a safe, reliable, and effective closure means which avoids some disadvantages of prior art cuffs. An object of this invention is to provide a cuff having a closure which securely closes the cuff without external sutures.

One aspect of the invention provides an implantable cuff comprising: a flexible tubular cuff member having longitudinal slit extending through a wall thereof, the slit having first and second edges; and a closure associated with the slit. The closure comprises: a pair of spaced apart first apertured members affixed to the cuff member at the first edge, the first apertured members having apertures aligned generally with the slit; a second apertured member capable of being interdigitated between the first apertured members and affixed to the cuff member at the second edge, the second apertured member having an aperture aligned generally with the slit; and an elongated locking member capable of being inserted to extend through the apertures of the first apertured members and the second apertured member when the second apertured member is interdigitated with the first apertured members.

In a preferred embodiment, the first and second apertured members comprise first and second tubes connected to the cuff member. In a further preferred embodiment the first tubes are resilient and the second tubes are spaced apart by distances slightly less than lengths of the first tubes so that, when the first and second tubes are interdigitated, the first and second tubes seal the slit closed.

Another aspect of the invention provides a cuff, as described above, further comprising a flexible flap extending across the slit. The flexible flap has an edge affixed to the cuff member along one of the first and second edges. Preferably the flap is radially inward from the first and second apertured members. In another embodiment of the invention, a second flap is provided on an outer surface of the cuff body to further seal the slit.

The invention also provides a method of providing an electrical connection to a body tissue, for example a nerve. the method comprises the steps of:

(a) Providing a cuff of a size suitable to envelop the body tissue, the cuff comprising: a cuff member having a longitudinal slit in a wall thereof; at least one electrode disposed on an inner surface of the cuff member; a sealing closure comprising a plurality of interdigitated apertured members attached to the cuff member on alternate sides of the slit and a locking member capable of being inserted through apertures in the apertured members to lock the cuff closed;

(b) Spreading sides of the slit apart and placing the cuff around the body tissue;

(c) Sealing the cuff around the body tissue by interdigitating the apertured members;

(d) Inserting the locking member through the apertures in the apertured members to lock the cuff closed; and (e) Extending an electrical connection to the electrode in the cuff.

BRIEF DESCRIPTION OF DRAWINGS

In drawings which illustrate specific embodiments of the invention, but which should not be construed as restricting the spirit or scope of the invention in any way.

DETAILED DESCRIPTION OF PREFERRED EMBODIMENT

Figure 10A:
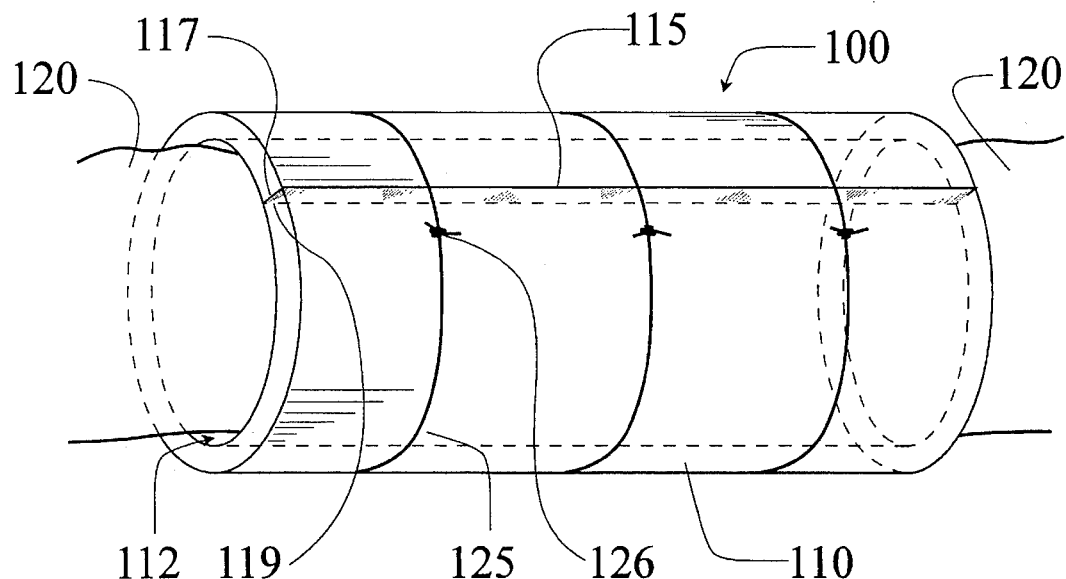
FIGS. 10A and 10B show respectively a prior art sutured cuff and a failure mode of a prior art sutured cuff.

FIG. 10A shows a prior art cuff 100. Cuff 100 comprises a tubular cuff member 110 having a central lumen 112. Cuff member 110 is made of a biologically compatible, flexible, resilient, insulating, material such as silicone rubber. Cuff member 110 has a longitudinal slit 115 extending through its wall. Cuff member 110 may be implanted around a piece of tissue, for example a nerve 120 by surgically exposing nerve 120, opening cuff member 110 by pulling apart edges 117 and 119 of slit 115, placing cuff member 110 around nerve 120 and bringing edges 117 and 119 together. Edges 117 and 119 tend to stay together because of the resilient nature of cuff member 110. Sutures 125 are then tied around cuff member 116 with knots 126 to seal edges 117 and 119 together.

Figure 10B:
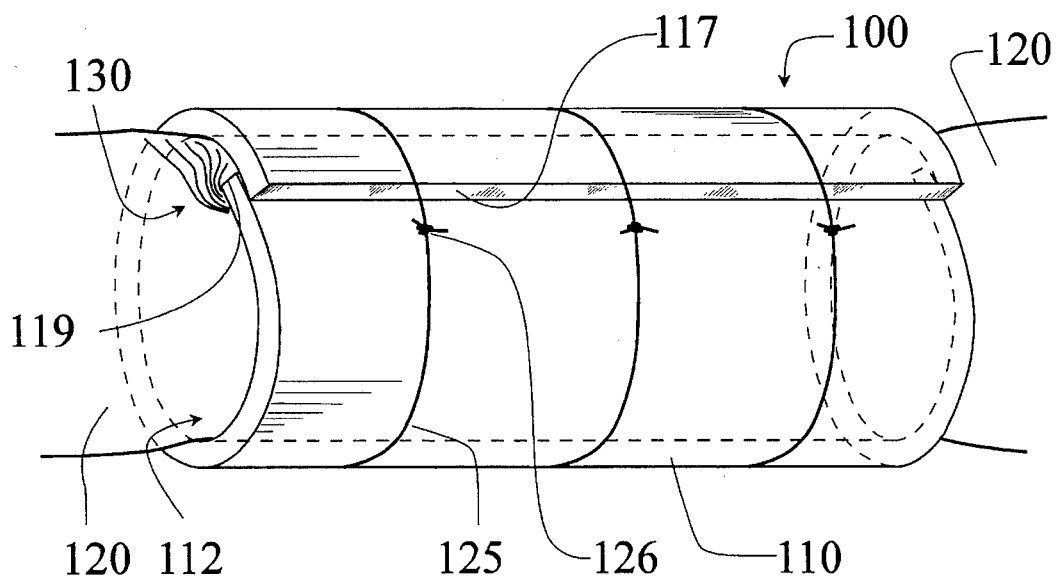

As shown in FIG. 10B, in a prior art cuff, edge 119 may slip with respect to edge 117. If this happens then the cross sectional area of lumen 112 is reduced. Nerve 120 may then be squeezed, as indicated at 130. This may damage nerve 120. Furthermore, any gap between edges 117 and 119 reduces the electrical and physical isolation of the portion of nerve 120 within cuff 100.

Figure 1:
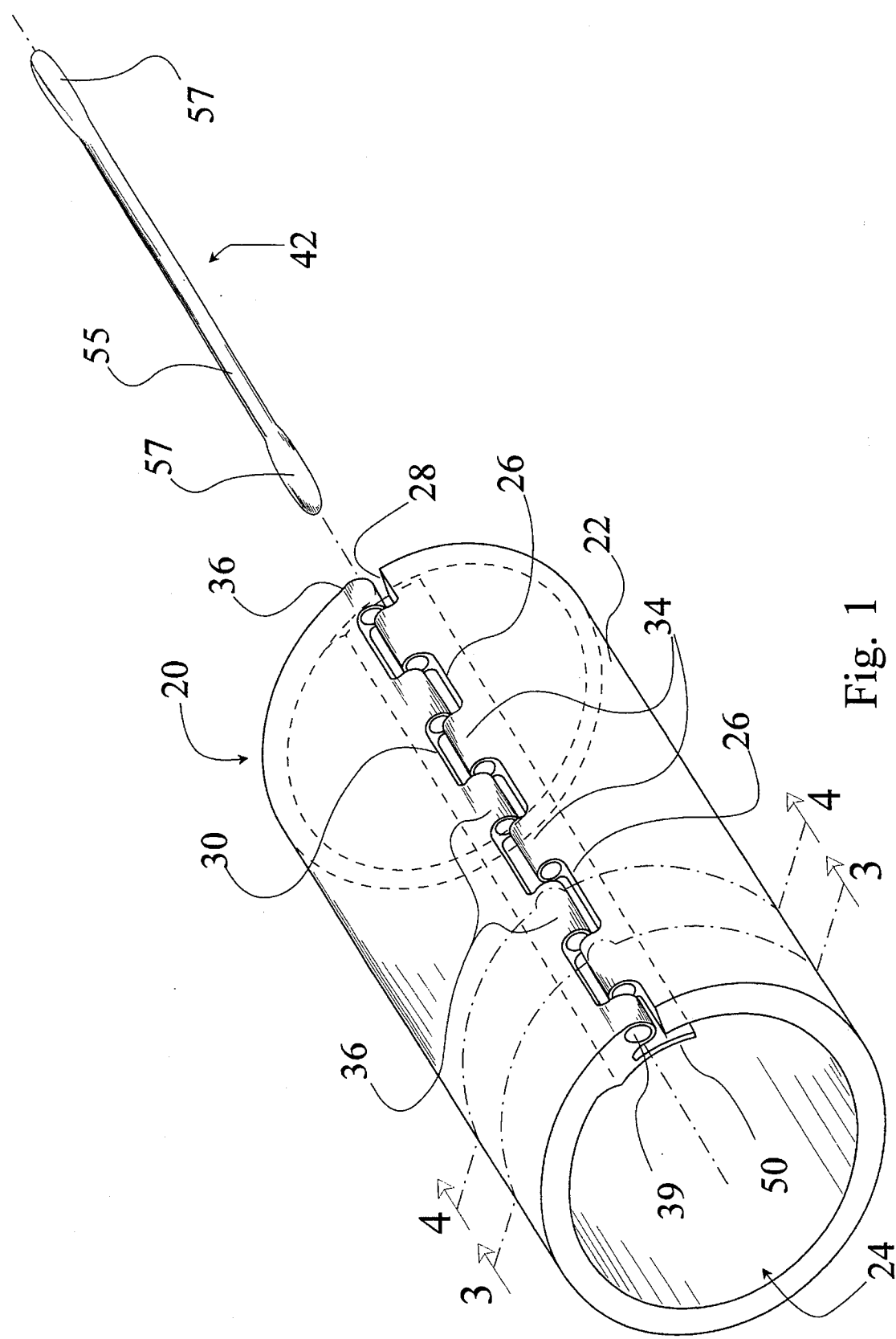
FIG. 1 is a diagrammatic perspective view of a nerve cuff according to the invention in a slightly opened position.

FIG. 1 shows a cuff 20 according to the invention. As described below, cuff 20 is adapted for use as a nerve cuff. However, those skilled in the art will appreciate that the cuff closure of the invention may be used to advantage in other implantable cuffs. Cuff 20 comprises a tubular cuff member 22 having a central lumen 24. Cuff member 22 is made of a biologically compatible, flexible, resilient, electrically insulating, material such as silicone rubber. For example, cuff member 22 may be a section of medical grade silicone tubing. Cuff member 22 has a longitudinal slit 26 extending through its wall. Slit 26 has a first edge 28 and a second edge 30.

Cuff 20 has a closure for fastening slit 26 closed. The closure comprises a plurality of interdigitated apertured members which are attached to cuff member 22 on alternate sides of slit 26 and one or more locking members 42 which can be passed through apertures in the apertured members to hold slit 26 closed. Preferably the closure further comprises a flap 50 to better seal slit 26.

The apertured members are preferably spaced so that, when they are interdigitated, they form a smooth, substantially sealing, closure of slit 26. This both improves the mechanical and/or electrical isolation of the inside of the cuff and provides no foothold for the growth of connective tissue. The apertured members preferably comprise a number of small tubes 34, 36 attached to cuff member 22 near, and preferably on, edges 28 and 30 of longitudinal slit 26.

Figure 2:
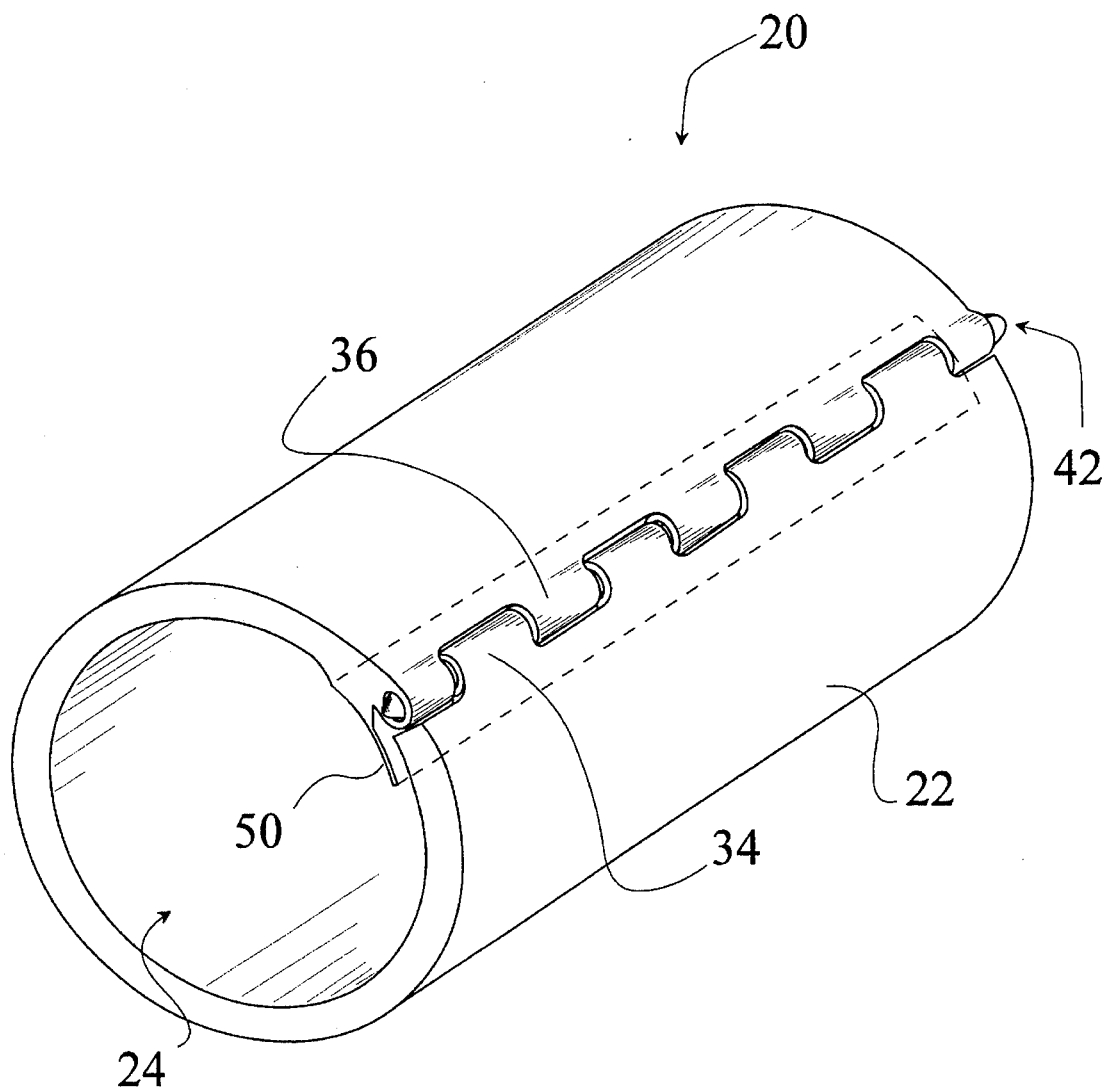
FIG. 2 is the nerve cuff of FIG. 1 in a closed and locked position.

First tubes 34 are attached to first edge 28 and second tubes 36 are attached to second edge 30. First tubes 34 are spaced apart along edge 30 by distances equal to, or very slightly less than, the lengths of second tubes 36. In this way, when cuff 20 is closed, as shown in FIG. 2, tubes 34 and 36 are interdigitated to form a substantially sealing closure of slit 26. In FIG. 1 cuff 20 is shown partially open, cuff 20 can be opened further by pulling apart edges 28 and 30.

Tubes 34 and 36 may be, for example, short sections of biologically compatible silicone tubing attached to edges 28 and 30 with a biologically compatible, flexible adhesive such as medical grade silicone adhesive. For example, stock No. MDX-4-4210 adhesive, which is manufactured by the Dow Corning Corporation of Midland, Mich. may be used. Where cuff member 22 is a slit section of resilient tubing and edges 28 and 30 are spread apart to receive tubes 34 and 36 then the resilience of cuff member 22 will tend to bias cuff 20 toward its closed position even when cuff 20 is already closed, which is advantageous.

An alternative method of making cuff 20 is to mould cuff member 22 and tubes 34, 36 together as a unit by injection moulding or another suitable industrial process. Preferably the cuff should be moulded such that a bias force tends to press edges 28, 30 together even when cuff 20 is closed. In the prior art cuff pictured in FIGS. 10A and 10B cuff member 110 provides very little, or no, force to bring edges 117 and 119 together when cuff 100 is closed. Any bias force comes from sutures 125.

Preferably cuff 20 has enough tubes 34, 36 and each of tubes 34, 36 is short enough, that forces are effectively distributed along the edges of slit 26. When cuff 20 is closed there should be no large gaps either between the ends of adjacent tubes 34, 36 or between tubes 34 or 36 and edges 30 or 28 respectively. Large gaps would compromise the electrical isolation of the interior of cuff 20 from the exterior. While a cuff could be made with as few as one tube 34 capable of being interdigitated between two tubes 36, preferably cuff 20 comprises at least three each of tubes 34 and 36. Preferably there are an odd number of tubes 34 if there are an even number of tubes 36 and vice versa.

Preferably the outside diameter of tubes 34, 36 is comparable to the wall thickness of cuff member 22. For example, if cuff member 22 is comprised of the stock No. SM-2150A silicone tubing available from Sil-Med Corporation of Taunton, Mass., which has a wall thickness of 0.81 mm, then tubes 34, 36 may be made from stock No. 602–135 silicone tubing available from Dow Corning Corporation of Midland, Mich. which has an external diameter of 0.9 mm.

This helps to ensure that, when closed, cuff 20 has a smooth outside circumference and overall shape.

As noted above, the closure further comprises a rod-like locking member 42 which can be passed through the bores 39 of tubes 34, 36 when cuff 20 is closed. When locking member 42 is in place, as shown in FIG. 2, cuff 20 cannot be opened. Locking member 42 prevents edges 28 and 30 from moving radially relative to each other. When locking member 42 is inserted through tubes 34 and 36 edges 28 and 30 are locked together so that opening, or inward spiralling of cuff 20 (as shown in FIG. 10B with respect to cuff 100) is prevented. Locking member 42 reduces the possibility that cuff 20 will crush a nerve inside cuff 20 through the action of internal or external forces.

Locking member 42 preferably has a shaft 55 having a diameter equal to or slightly smaller than the bores of tubes 34, 36. For example if tubes 34, 36 have bores with an internal diameter of 0.5 mm then shaft 55 preferably has an outer diameter in the range of 0.4 mm–0.5 mm. Preferably the ends 57 of locking member 42 are tapered and are slightly larger in diameter than shaft 55. Ends 57 may be, for example, moulded with a biologically compatible epoxy such as AQUATAPOXY™ from American Chemical Corp. of St. Louis, Mo. Ends 57 help to keep locking member 42 in place within tubes 34, 36 when cuff 20 is closed and locked. Ends 57 should be small enough and shaped so that locking member 42 is sufficiently easy to insert or remove in a surgical setting but should be a tight enough fit in tubes 34, 36 that locking member 42 will not slip out of tubes 34, 36 after implantation.

Locking member 42 is preferably made of a non-conductive, impermeable material such as teflon rod or a length of monofilament suture material. Locking member 42 should be stiff enough to insert through the bores of tubes 34, 36 without excessive bending, although locking member 42 should ideally be of comparable flexibility to the overall cuff 20. An alternative material for locking member 42 is implantable grade stainless steel tubing, for example 0.4 mm internal diameter hypodermic stainless steel tube, Catalog No. 8332 from A-M Systems Inc. of Everett, Wash. Stainless steel tubing has excellent properties of biological compatibility, strength, and lifetime. However, stainless steel tubing may reduce electrical isolation because it is electrically conductive and is somewhat stiffer than is generally preferable.

A flap 50 is optionally, but preferably, provided on the inside of slit 26 to further seal and electrically insulate the closure of slit 26. If cuff 20 is to be used to enclose electrodes for extremely sensitive electrical measurements or if it is necessary to provide a tight seal against fluid flow then flap 50 will likely be required. Flap 50 will also be required if the apertured members used in the closure have spaces between them so that the apertured members do not provide sufficient, or any, sealing.

Figure 3:
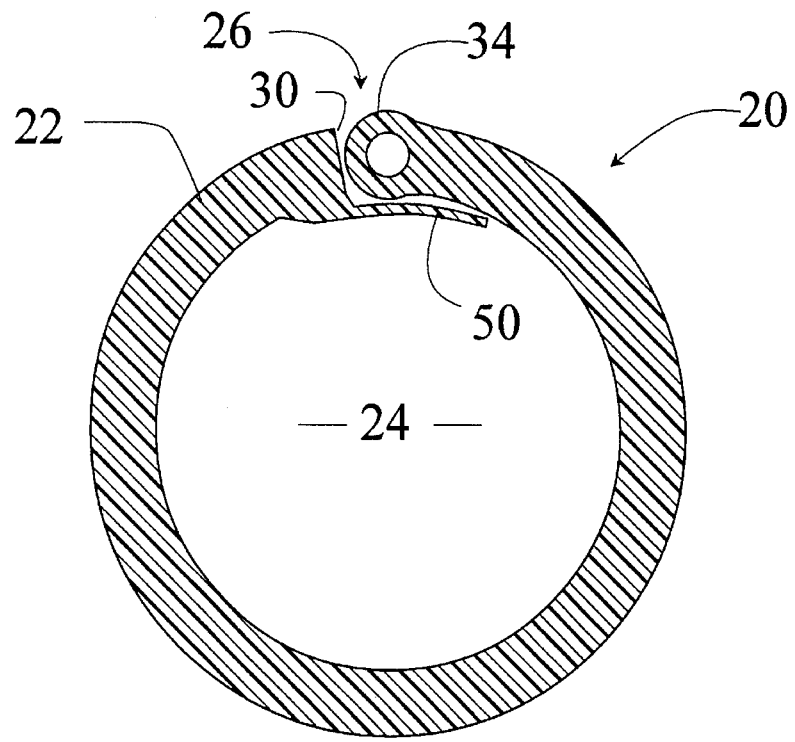
FIG. 3 is a section in the plane 3—3 of the nerve cuff of FIG. 1.
Figure 4:
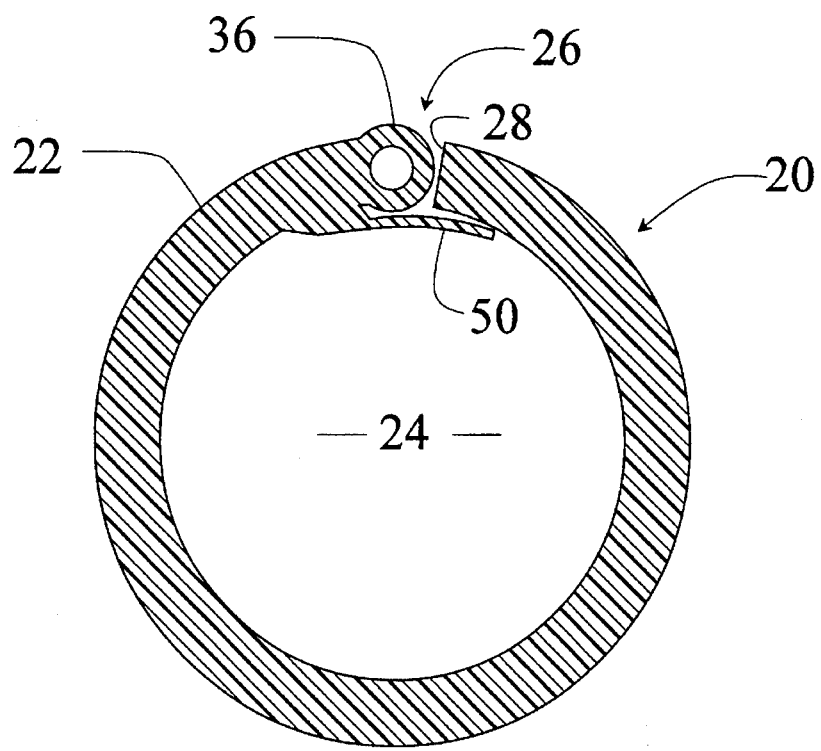
FIG. 4 is a section in the plane 4—4 of the cuff of FIG. 1.

The construction of flap 50 and the relationship of tubes 34, 36 to edges 28, 30 and flap 50 are shown in FIGS. 3 and 4, which are cross-sections of cuff 20. Flap 50 preferably comprises an electrically insulating, flexible, fluid impervious, biologically compatible material such as silicone sheeting. Flap 50 helps to seal slit 26 both electrically and mechanically. Because flap 50 is fluid impervious, it acts to restrict fluid movement and inhibits the growth of tissue through slit 26. Preventing tissue from growing into slit 26 also helps to maintain the electrical isolation of lumen 24 from the exterior of cuff 20. The electrically insulating nature of flap 50 also improves the electrical characteristics of the cuff for both nerve stimulation and nerve recording applications.

Flap 50 generally has a length approximately equal to the length of cuff 20 and has a width sufficient to overlap both edges 28 and 30 of longitudinal slit 26 when cuff 20 is closed. Flap 50 should be thin enough to easily conform to the inside surface of cuff 20 yet thick enough to provide both electrical and mechanical isolation. For example 0.125 mm thick SILASTIC™ silicone sheeting Catalog No. 500-1 from Dow Corning Corporation of Midland, Mich. is a suitable material for flap 50 for most nerve cuff applications.

As shown in FIGS. 3 and 4, flap 50 is affixed to cuff member 22 on only one side of the slit 26. If, as is preferred, the endmost tubes of cuff 20 are both attached to the same side of slit 26 then it may be advantageous to have flap 50 extend from the other side of slit 26. Flap 50 may be affixed to cuff member 20 with a suitable adhesive as described above with respect to tubes 36 and 38. Flap 50 may also be moulded together with cuff member 20 as described above. If tissue grows within lumen 24 of cuff 20 then flap 50 is forced tighter against slit 26 and cuff member 22. This provides an advantage over the prior art cuffs discussed above, where tissue growth in the lumen of the cuff tends to open the cuff.

Figure 5:
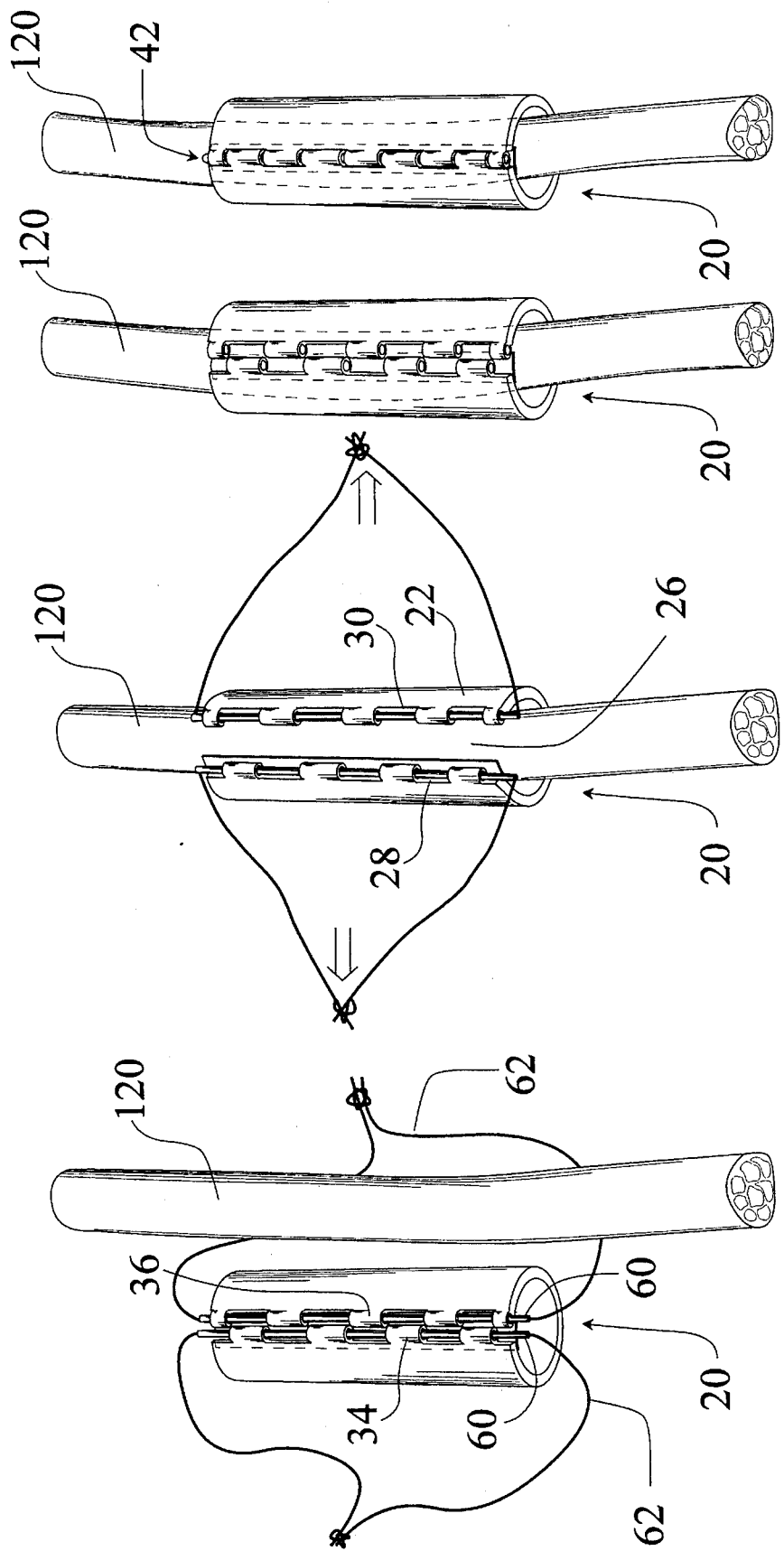
FIGS. 5A, 5B, 5C and 5D illustrate the steps in a procedure for installing a cuff according to the invention.

Cuff 20 may be surgically implanted around a peripheral nerve 120 as shown in FIGS. 5A through 5D. Cuff 20 is preferably equipped, prior to its packaging and sterilization, with means to assist a user to open cuff 20. For example, as shown in FIG. 5A, rigid pins 60 may be inserted through the bores of tubes 34 and the bores of tubes 36. Sutures 62 attached to pins 60 server as handles for opening the cuff. As shown in FIG. 5A, peripheral nerve 120 is first surgically exposed and mobilized. One of sutures 62 is passed underneath nerve 120. Next cuff 20 is carefully positioned under the mobilized nerve 120. Cuff 20 is then opened, as shown in FIG. 5B, by pulling on sutures 62 to draw edges 28 and 30 of cuff member 22 apart. When edges 28 and 30 are far enough apart, nerve 120 is allowed to gently fall into the inside of cuff 20 (FIG. 5B). Sutures 62 are then cut, pins 60 are removed, and cuff 20 is carefully closed taking care to align tubes 34 with tubes 36. FIG. 5C shows cuff 20 with tubes 34 aligned with the spaces between tubes 36 just before cuff 20 is fully closed. Tubes 34 are then interdigitated with tubes 36. When cuff 20 is closed, only the elastic properties of the cuff member 22 and friction between the ends of tubes 34 and the ends of tubes 36 holds cuff 20 closed. Finally, as shown in FIG. 5D, locking member 42 is inserted through the bores of all of tubes 34 and 36, thereby ensuring permanent closure of cuff 20.

Cuff 20 can be removed from a body more safely and with less trauma after a long implantation than the prior art cuffs described above. The sutures in prior art cuffs can attract excessive connective tissue growth. This can make it difficult to surgically mobilize and clear debris from prior art cuffs prior to removal. There are no sutures or large apertures on the exterior surface of cuff 20 to attract connective tissue growth. Thus, cuffs 20 are relatively easy to remove after implantation. For example, cuffs substantially as shown in FIG. 1 were implanted for six months around various nerves in cats. By the time the cuffs were removed, a fine, uniform, layer of connective tissue had sealed the smooth outer surfaces of the cuffs. After the connective tissue was detached from the exterior of a cuff it was easy to slip locking member 42 out of tubes 34 and 36. Tubes 34 and 36 were then gently manipulated apart to open the cuff and to safely remove the cuff from around the nerve.

As noted above, nerve cuffs can be used to stimulate nerves or to record electrical signals in nerves by providing electrodes in the cuff. Nerve cuffs for recording nerve electrical activity or stimulating a nerve have particular requirements which are not necessary in other types of cuff. In a nerve cuff for recording, the cuff material, size and the closure of the cuff must provide sufficient electrical isolation from the outside environment that the very small action currents produced by nerve axons can be resolved. A recording nerve cuff must ideally completely surround the selected nerve so that local current density changes associated with nerve impulses can be detected as voltage differences between two or more circumferential recording electrodes. For nerve stimulation purposes the nerve cuff must provide enough electrical isolation that the stimulation signal can develop a sufficient electrical charge density inside the cuff to depolarize the nerve to threshold.

To improve resolution of nerve signals and also to maximally reject the pickup of unwanted signals generated by muscles and other sources outside the cuff, a nerve recording cuff should completely envelop the nerve in question. The nerve cuff should be sealed and electrically insulating, particularly in a central region surrounding the recording electrode(s). Preferably the cuff should have an internal diameter approximately 10–20% greater than the diameter of the nerve to be enveloped and should typically have a length approximately ten times its internal diameter.

Figure 6:
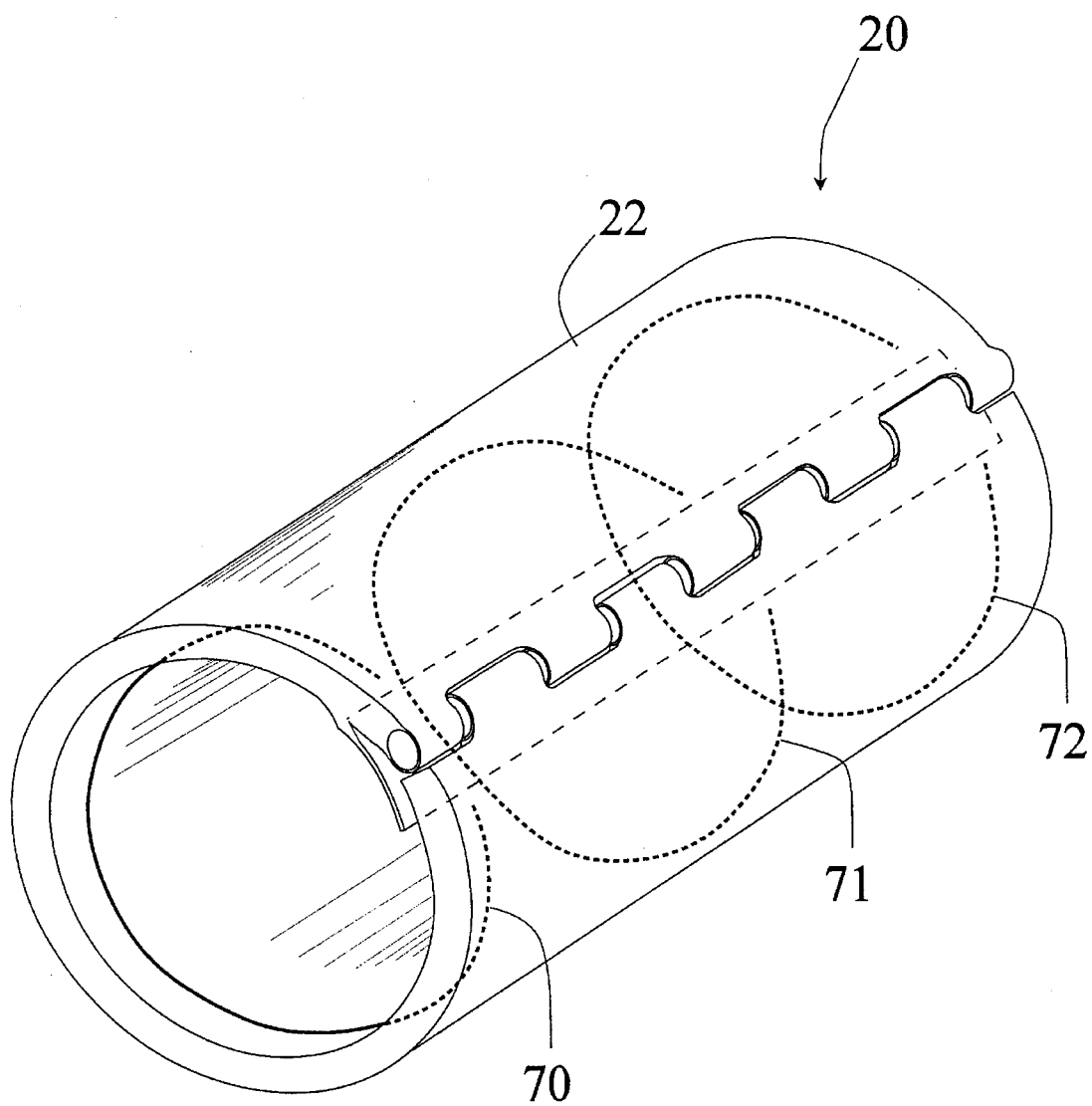
FIG. 6 is a view of a nerve cuff according to the invention equipped with near-circumferential electrodes for measuring electrical activity of tissues inside the cuff or for electrically stimulating tissues inside the cuff.

FIG. 6 shows a cuff 20 incorporating the improved closure of the invention adapted by the addition of three near-circumferential electrodes 70, 71, 72 for recording nerve electrical signals and/or for electrically stimulating a nerve. Electrodes 70, 71, 72 may be wires sewn into cuff member 22 tubing, deposited by thin film or electrostatic processes on the inner surface cuff member 22 or otherwise attached to cuff 20. Electrodes 70, 71, 72 are made of a biologically compatible, electrically conductive material such as stainless steel, platinum, or iridium and are preferably flexible. For recording nerve signals, outer electrodes 70 and 72 are preferably shorted together to act as a reference electrode. Middle electrode 71 can then be used as a recording electrode. Neural signals are then measured as voltage differences between electrode 71 and electrodes 70 and 72. In a stimulating application, middle electrode 71 is typically used as a cathode for a stimulus pulse and one or both of outer electrodes 70, 72 is used as an anode.

Figure 7:
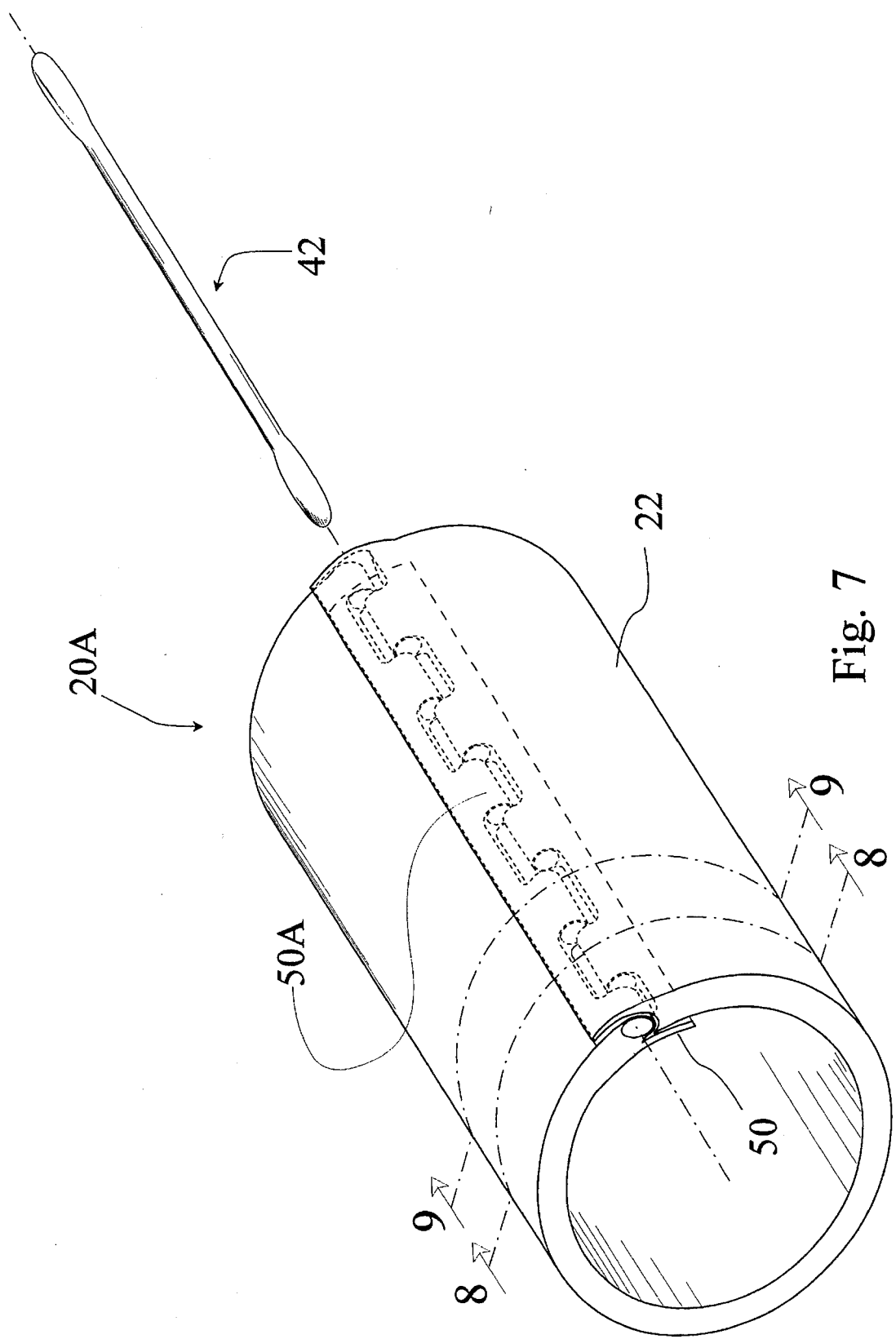
FIG. 7 is a perspective view of a cuff according to an alternative embodiment of the invention having an additional outside flap.
Figure 8:
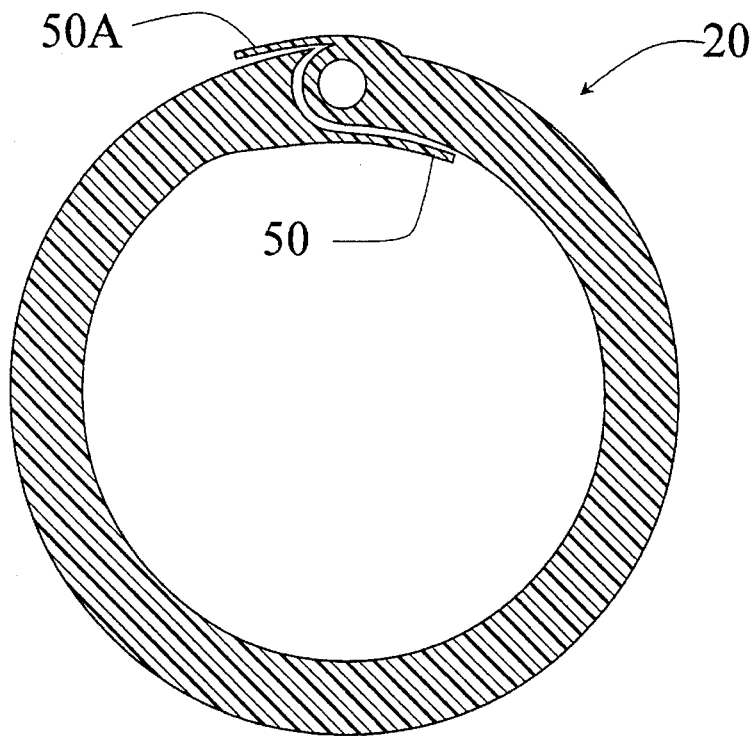
FIG. 8 is a section in the plane 8—8 of the cuff of FIG. 7.
Figure 9:
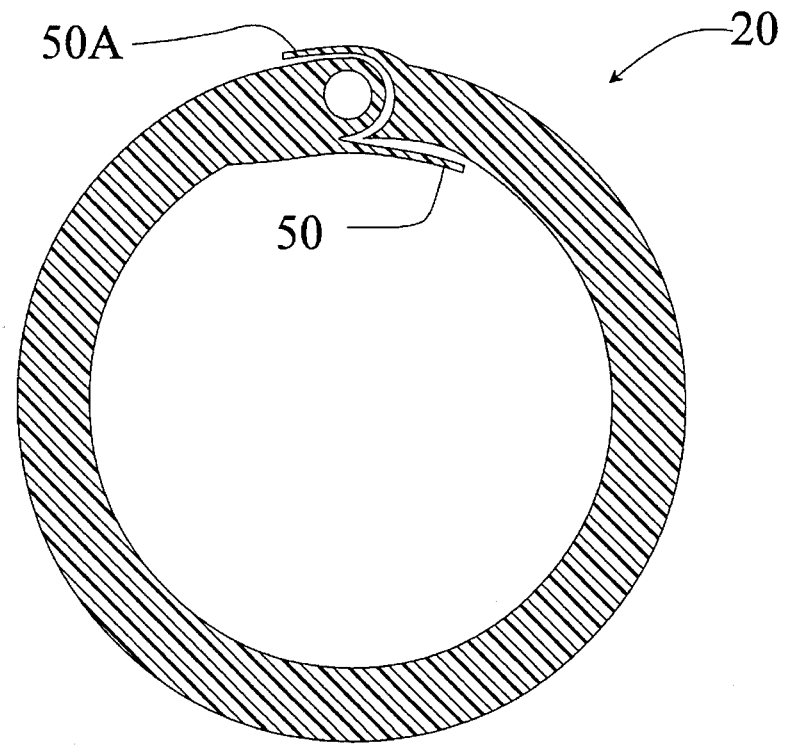
FIG. 9 is a section in the plane 9—9 of the cuff of FIG. 7.

FIGS. 7–9 show an alternative cuff 20A which comprises an outer flap 50A in addition to, or, less preferably, in substitution for, inner flap 50. Outer flap 50A serves to further mechanically, or mechanically and electrically, isolate lumen 24 of cuff 20A from the exterior of cuff 20A. Outside flap 50A preferably comprises a non-conductive, flexible, biologically compatible material such as silicone, and acts to prevent fluid flow and tissue growth into interdigitated tubes 34, 36 from the exterior of cuff 20A. Outside flap 50A spans tubes 34, 36 along the entire length of cuff 20A and may be mechanically biased to conform to the curvature of cuff 20A. Preferably, outer flap 50A is fabricated from silicone sheeting as described above with respect to flap 50. Outer flap 50A may be attached to cuff member 22 with a suitable adhesive. Outside flap 50A may alternatively be formed in an injection moulding process as described above. Outside flap 50A may be attached to cuff member 22 on either the same side of slit 26 as flap 50 or on opposite sides as illustrated in FIGS. 7, 8, and 9.

It will be readily understood that a cuff according to the invention can be used in place of prior art nerve cuffs in applications other than those described above. For example, a nerve cuff 20 according to the invention could be used in place of prior art nerve cuffs to deliver pharmacological agents to a section of nerve inside the cuff or to act as a stable mounting platform on which to place fragile micro-electrodes for stimulation and/or recording of electrical activity in single axons.

As will be apparent to those skilled in the art in the light of the foregoing disclosure, many alterations and modifications are possible in the practice of this invention without departing from the spirit or scope thereof. For example, while it is not preferred, the apertured members in the closure could be small, separated, tings attached alternately to sides 28 and 30 of slit 26 instead of sections of tubing, as described above. As another alternative, tubes 34 and/or 36 could be formed by folding sheets of a suitable bio-compatible material, such as thin silicone sheeting, over edges 28 and 30 of slit 26, fastening the edges of the sheeting to cuff member 22, and cutting notches in the folded edges of the sheeting. The sheeting remaining between the notches would form tube-like loops projecting past edges 28 and 30. As a further alternative, tubes 34 and/or 36 could be formed by folding a piece of sheeting upon itself and attaching the two sides of the sheeting together, for example with a suitable adhesive, to form a tube running along the folded over edge and a flap extending along the tube. The folded over edge could then be notched, as described above, to form a series of spaced apart tube-like segments and the flap could be attached to cuff member 22.

Figure 11A:
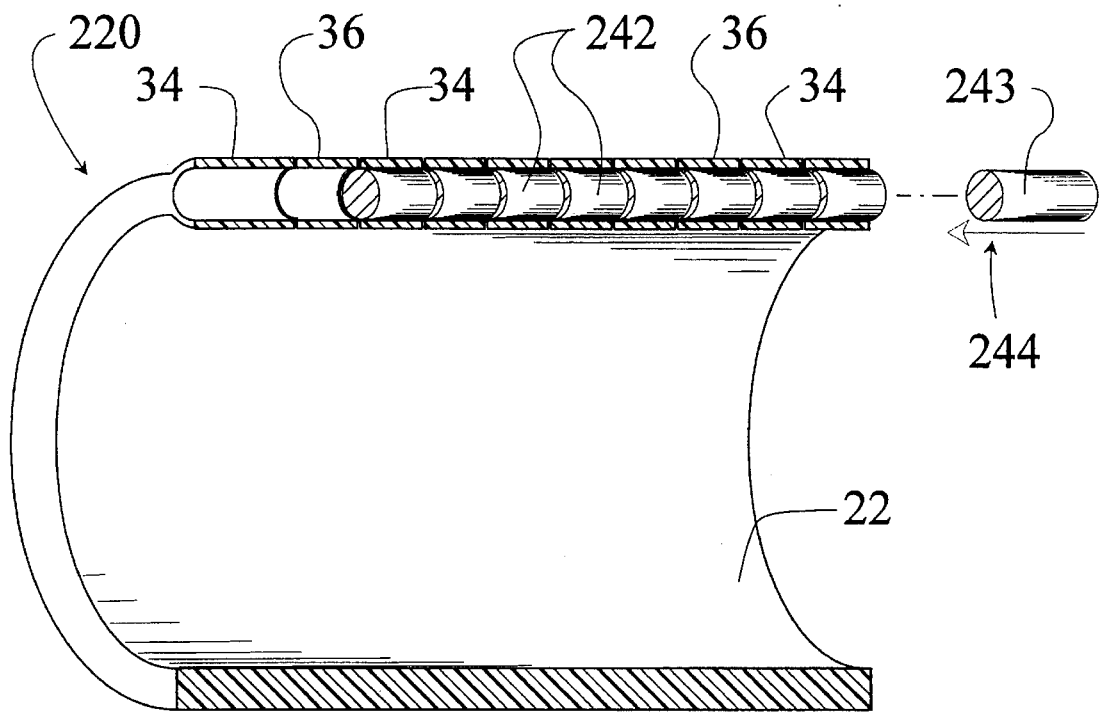
FIGS. 11A and 11B are sections through a cuff according to the invention having an alternative closure with multiple locking members.
Figure 11B:
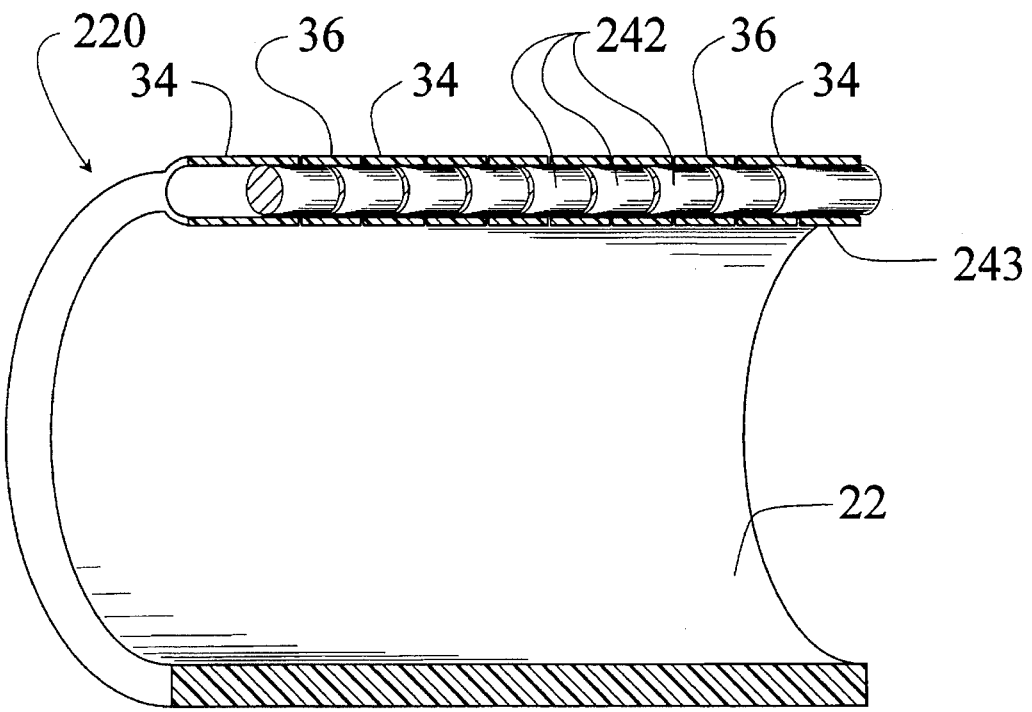

More than one locking member 42 may be used. For example, two short locking members 42 could be used, one inserted from each end of cuff 20. In an alternative embodiment of the invention, which is shown in FIGS. 11A and 11B the locking member comprises multiple locking member segments 242, 243. FIG. 11A shows a cuff 220 in a closed, but not locked, configuration. A short locking member segment 242 is aligned inside each of tubes 34, 36 (with the possible exception of two tubes at one end of cuff 220). Locking member segments 242 are the same length as tubes 34, 36. Because locking member segments 242 do not cross between tubes 34 and tubes 36 they do not interfere with closing cuff 220. Cuff 220 can be locked by inserting a locking member segment 243 into a tube 36 at one end of cuff 220 as indicated by arrow 244. As locking member segment 243 is inserted it pushes locking member segments 242 so that each locking member segment 242 extends between a tube 34 and a tube 36. Locking member segment 243 is approximately 1½ times as long as tubes 34, 36 (or n+½ times as long as tubes 34, 36 where n is an integer). As shown in FIG. 11B, after locking member segment 243 is inserted, cuff 220 is locked. The advantage of this embodiment is that locking member segment 243 can be much shorter than the unitary locking member 42 described above. Therefore, it can be easier to manipulate locking member segment 243 in tight quarters than it would be to insert a unitary locking member 42. A disadvantage of this embodiment is that a locking means comprising segments 242, 243 may not provide secure locking as would a longer unitary locking member 42, it may also be more difficult to sterilize the cuff with locking member segments 242 inserted, and segments 242 could cause problems if they escape during implantation or removal of the cuff, consequently, this embodiment is not preferred.

Accordingly, the scope of the invention is to be construed in accordance with the substance defined by the following claims.

We claim:

1. An implantable cuff comprising:
   (a) a flexible tubular cuff member having a longitudinal slit extending through a wall thereof, said slit having first and second edges; and
   (b) a closure associated with said slit, said closure comprising:
      (i) two or more spaced apart first apertured members affixed to said cuff member at said first edge, said first apertured members having apertures aligned generally with said slit; and
      (ii) a second apertured member interdigitated between two of said first apertured members and affixed to said cuff member at said second edge, said second apertured member having an aperture aligned generally with said slit
   (c) retaining means for maintaining said closure closed with at least one said second apertured member interdigitated between said first apertured members.

2. The implantable cuff of claim 1 wherein said retaining means comprises an elongated locking member inserted to extend through said apertures of said first apertured members and said second apertured member when said second apertured member is interdigitated with said first apertured members.

3. The implantable cuff of claim 2 wherein said locking member comprises a semi-rigid rod.

4. The implantable cuff of claim 3 wherein said locking member comprises a semi-rigid rod, said rod comprising a central portion having a diameter no greater than internal diameters of said apertures in said first and second apertured members and tapered end portions having diameters greater than said diameter of said central portion of said rod.

5. The implantable cuff of claim 2 wherein said locking member comprises a length of suture material.

6. The implantable cuff of claim 2 wherein said locking member comprises a plurality of axially aligned rod members.

7. The implantable cuff of claim 2 wherein said first apertured members comprise first tubes connected to said cuff member.

8. The implantable cuff of claim 7 comprising a plurality of second aperture member spaced apart by distances generally equal to lengths of said first tubes.

9. The implantable cuff of claim 8 wherein said second apertured members comprise second tubes connected to said cuff member.

10. The implantable cuff of claim 9 wherein said first and second tubes comprise flexible sheets folded over along a fold line and notched along said fold line.

11. The implantable cuff of claim 9 wherein said first tubes are resilient and said second tubes are spaced apart by distances slightly less than said lengths of said first tubes wherein, when said first and second tubes are interdigitated, said first and second tubes seal said slit closed.

12. The implantable cuff of claim 11 comprising at least three of said second tubes interdigitated with at least three of said first tubes.

13. The implantable cuff of claim 12 further comprising a flexible flap extending across said slit, said flexible flap having an edge affixed to said cuff member along one of said first and second edges.

14. The implantable cuff of claim 13 wherein said flap extends from said cuff member substantially along an entire length of said slit and said cuff is radially inward from said first and second apertured members.

15. The implantable cuff of claim 14 further comprising a second flap extending from an outer surface of said cuff member across said slit.

16. The implantable cuff of claim 1 further comprising a flexible flap extending across said slit, said flexible flap having an edge affixed to said cuff member along one of said first and second edges.

17. The implantable cuff of claim 16 wherein said flap extends from said cuff member substantially along an entire length of said slit.

18. The implantable cuff of claim 17 wherein said flap is radially inward from said first and second apertured members.

19. The implantable cuff of claim 18 further comprising a second flexible flap extending across said slit, said second flexible flap having an edge affixed to said cuff member along one of said first and second edges, wherein said second flexible flap is radially outward from said first and second apertured members.

20. The implantable cuff of claim 17 wherein said flap is radially outward from said first and second apertured members.

21. The implantable cuff of claim 17 wherein said retaining means comprises an elongated locking member inserted to extend through said apertures of said first apertured members and said second apertured member when said second apertured member is interdigitated with said first apertured members and said locking member comprises a semi-rigid rod.

22. The implantable cuff of claim 21 wherein said locking member comprises a semi-rigid rod, said rod comprising a central portion having a diameter no greater than internal diameters of said apertures in said first and second apertured members and tapered end portions having diameters greater than said diameter of said central portion of said rod.

23. The implantable cuff of claim 17 wherein said retaining means comprises an elongated locking member inserted to extend through said apertures of said first apertured members and said second apertured member when said second apertured member is interdigitated with said first apertured members and said locking member comprises a length of suture material.

24. The implantable cuff of claim 1 comprising at least three of said second apertured members interdigitated with at least three of said first apertured members.

25. The implantable cuff of claim 1 further comprising an electrode inside said cuff member.

26. The implantable cuff of claim 25 wherein said electrode is a near circumferential electrode centrally located on an inner surface of said cuff member.

27. The implantable cuff of claim 25 wherein said electrode comprises a biologically compatible electrically conductive material deposited on an inner surface of said cuff member.

28. The implantable cuff of claim 1 further comprising a catheter extending through said wall of said cuff member for introducing fluids into said cuff member.

29. A method for releasably enclosing a section of internal body tissue, said method comprising the steps of:

(a) surgically separating said section of internal body tissue from surrounding tissues;

(b) providing a tubular cuff comprising
  (i) a flexible tubular cuff member having a longitudinal slit extending through a wall thereof, said slit having first and second edges; and
  (ii) a closure associated with said slit, said closure comprising:
    (A) a pair of spaced apart first apertured members affixed to said cuff member at said first edge, said first aperture members having apertures aligned generally with said slit;
    (B) a second apertured member interdigitated between said first apertured members and affixed to said cuff member at said second edge, said second apertured member having an aperture aligned generally with said slit; and
    (C) an elongated locking member inserted to extend through said apertures of said first apertured members and said second apertured member when said second apertured member is interdigitated with said first apertured members;

(c) opening said cuff by drawing said first and second edges of said slit apart;

(d) placing said section of internal body tissue in said cuff;

(e) closing said cuff by interdigitating said second apertured member between two of said first apertured members; and (f) securing said cuff around said internal body tissues by passing a locking member through said apertures in said first and second apertured members.

30. The method of claim 29, further comprising the step of providing an electrical connection to said internal body tissue by extending an electrical conductor to at least one electrode disposed on an inner surface of said cuff member.

* * * * *